United States Patent [19]

Rai et al.

[11] Patent Number: 4,996,421

[45] Date of Patent: Feb. 26, 1991

[54] METHOD AND SYSTEM OF GEOPHYSICAL EXPLORATION

[75] Inventors: Chandra S. Rai; Carl H. Sondergeld, both of Tulsa, Okla.

[73] Assignee: Amoco Corporation, Chicago, Ill.

[21] Appl. No.: 264,926

[22] Filed: Oct. 31, 1988

[51] Int. Cl.$^5$ ............................................. G01N 21/35
[52] U.S. Cl. ..................................... 250/255; 250/253
[58] Field of Search ................... 250/253, 255; 378/45, 378/53, 88

[56] References Cited

U.S. PATENT DOCUMENTS

| | | | |
|---|---|---|---|
| 2,458,093 | 1/1949 | Muskat et al. | 73/153 |
| 2,531,083 | 11/1950 | Smith | 73/19 |
| 2,613,250 | 10/1952 | Bilhartz et al. | 324/65 R |
| 4,510,573 | 4/1985 | Boyce et al. | 364/498 |
| 4,593,195 | 6/1986 | Bienfait et al. | 250/253 |
| 4,616,134 | 10/1986 | Pruett et al. | 250/255 |
| 4,623,792 | 11/1986 | Böhme et al. | 250/255 |
| 4,839,516 | 6/1989 | Freeman et al. | 250/255 |

FOREIGN PATENT DOCUMENTS

| | | | |
|---|---|---|---|
| 2135049 | 8/1984 | United Kingdom . | |
| 2157423 | 10/1985 | United Kingdom | 250/255 |
| 2192056 | 12/1987 | United Kingdom . | |
| 8202573 | 8/1982 | World Int. Prop. O. | 250/255 |

OTHER PUBLICATIONS

J. Espitalié, B. Durand, J.-C. Roussel and C. Souron, "Étude de la Matière Organique Insoluble (Kérogène) des Argiles du Toarcien du Bassin de Paris; Deuxième partie: Étude en Spectroscopie Infrarouge, en Analyse Thermique Différentielle et en Analyse Thermogravimétrique" Revue de l'Institut Francais du Petrole, vol. 28, No. 1, (Jan.–Feb. 1973) pp. 37–66.

Primary Examiner—Constantine Hannaher
Attorney, Agent, or Firm—Timothy D. Stanley; Marcy M. Lyles

[57] ABSTRACT

A system and method of geophysical exploration is described whereby composition logs of the minerals comprising the formations surrounding a wellbore can be obtained. Samples of the formations surrounding a wellbore are obtained at selected intervals along the length of the wellbore. Each of the core samples is irradiated with electromagnetic radiation and a spectral response signal, representative of the electromagnetic response of each sample to the electromagnetic radiation is recorded. Peaks in the spectral response signals are located and correlated with minerals exhibiting similar electromagnetic characteristic response peaks. Since the samples were obtained from known depths within the wellbore, a composition log of the minerals comprising the formations surrounding the wellbore can be prepared displaying the minerals identified as a function of depth in the wellbore.

14 Claims, 5 Drawing Sheets

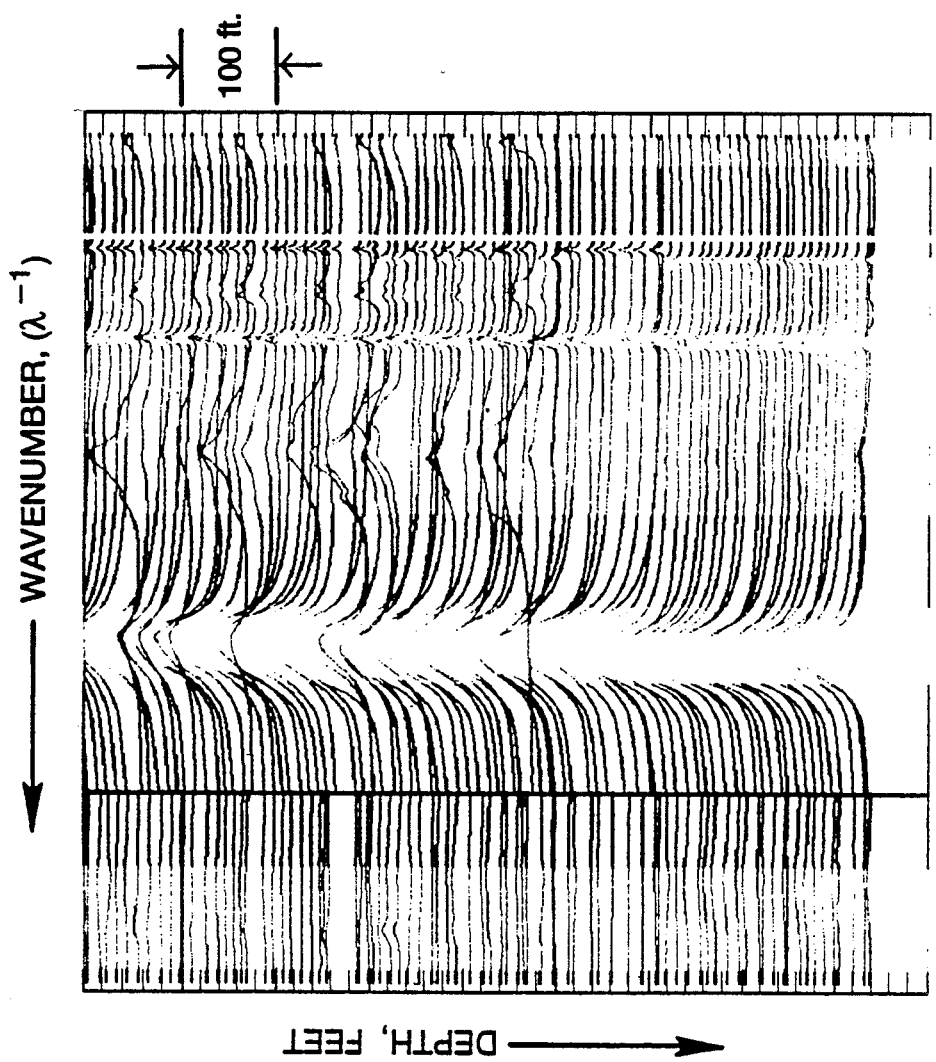
FIG.4
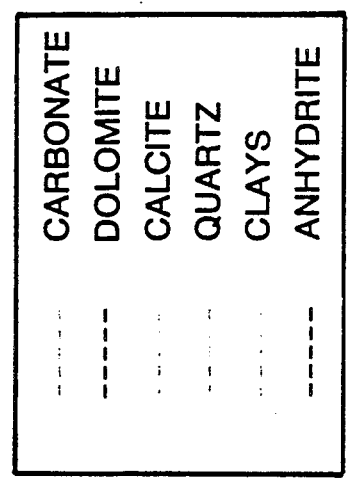

METHOD AN SYSTEM OF GEOPHYSICAL EXPLORATION

BACKGROUND OF THE INVENTION

The present invention relates generally to a method and system of geophysical exploration and more particularly to a method and system for obtaining a composition log of the minerals comprising the earth's subterranean formations surrounding a wellbore.

In the continuing search for oil and gas, explorationists have developed a wide array of geophysical exploration methods for imaging the earth's subterranean formation structures and displaying those images as well as providing estimates of selected formation characteristics such as lithology, porosity, density, and velocity of propagation of seismic energy in the earth's formations. Exemplary of such geophysical exploration methods are seismic surveys, gravity surveys, magnetic surveys, acoustic logging, resistivity logging and neutron logging.

Occasionally, core samples are obtained from regions of interest within a limited portion of the wellbore for transport to a central laboratory so that properties of the formations adjacent the borehole, such as fluid content of the sample, (U.S. Pat. No. 2,458,093), oil content of the sample (U.S. Pat. No. 2,531,083), and resistivity of the sample (U.S. Pat. No. 2,613,250) can be obtained. Additionally, analyses of such core samples to determine mineralogy have been undertaken at remote laboratory facilities. Unfortunately, such core samples generally represent only a small fraction of the formation lithologies traversed by the wellbore along its length and as such the measured properties represent only a small fraction of the earth's formations surrounding the wellbore.

During the drilling process, chips which have broken away from the subsurface formations can be captured from the drilling fluid at the surface for analysis. Typically, explorationists have identified the lithologies of the subsurface formations from such chips. However, determining the exact depth in the wellbore from which the chips originated is generally not possible due to the very nature of their transport to the surface. Consequently, core samples and chip samples fail to provide either a regular sampling of borehole formation lithologies along the length of the wellbore or fail to accurately determine the depth of origin of such samples so that logs of formation characteristics, as a function of depth over generally the entire wellbore length, cannot be produced. Moreover, the very nature of the chip samples can often times preclude measuring certain formation characteristics (for example, measurement of seismic velocity or compressive strength).

In view of such difficulties, the present invention provides a novel method of geophysical exploration whereby a composition log of the minerals comprising the formations surrounding a wellbore can be obtained. With such composition logs, explorationists can better evaluate the results of geophysical surveys and thus better evaluate the oil- and gas-bearing potential of such formations.

SUMMARY OF THE INVENTION

The present invention provides a novel method of geophysical exploration whereby a composition log of the minerals comprising the formations surrounding a wellbore can be obtained. With such composition logs, explorationists can better evaluate the results of geophysical surveys and thus better evaluate the oil- and gas-bearing potentials of such formations.

Samples of the earth's formations surrounding a wellbore are obtained at selected intervals along the length of the wellbore. Each of the samples is irradiated with electromagnetic radiation and a spectral response signal, representative of the electromagnetic radiation response of each sample, is recorded. Peaks in the spectral response signals are located and correlated with minerals exhibiting similar electromagnetic characteristic response peaks. Since the samples were obtained from known depths within the wellbore, a composition log of the minerals comprising the formations surrounding the wellbore can be prepared displaying the minerals identified as a function of depth in the wellbore.

In one embodiment of the invention, the samples are irradiated with infrared radiation and a spectral response signal is obtained which is representative of the infrared radiation absorbed by each sample. The spectral location and amplitude of each characteristic peak in the spectral response signal can be obtained. By correlating the spectral location of the characteristic peaks in the spectral response signal of each sample with minerals exhibiting similar characteristic peaks, a qualitative measure can be obtained of the minerals comprising the formation surrounding the wellbore as represented in each sample. By employing the spectral location and relative amplitude of the characteristic peaks, a regression analysis can be performed using the spectral locations and relative amplitudes of a plurality of samples with known compositions to determine a quantitative measure of the minerals in each sample.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 4 is a color drawing of a composition log of subterranean formations around a wellbore;

DETAILED DESCRIPTION OF THE INVENTION

The present invention relates generally to a method of geophysical exploration and more particularly to a method and system for obtaining a composition log of the minerals comprising the earth's formation surrounding a wellbore.

Figure 1:
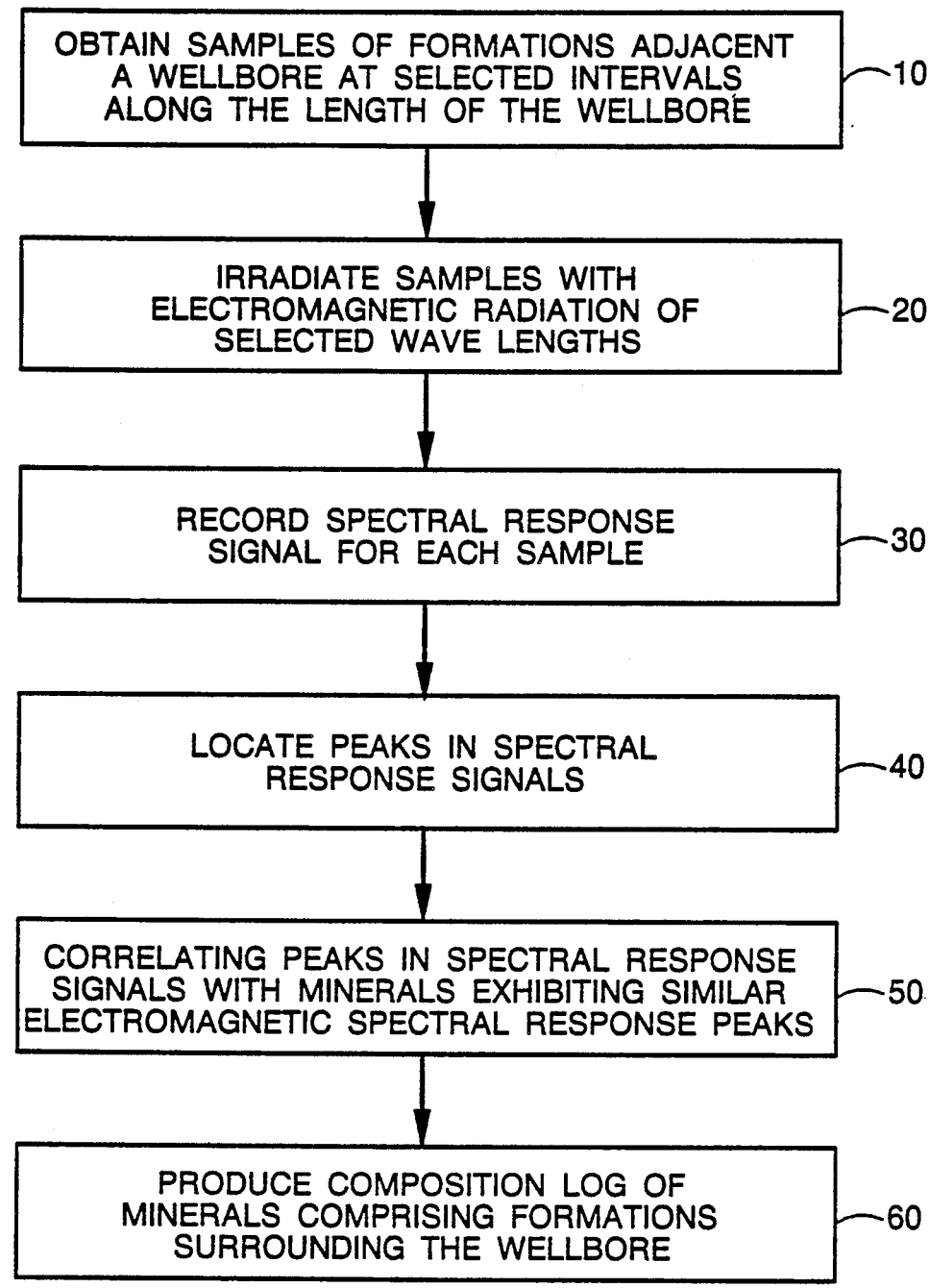
FIG. 1 is a flow diagram of the present invention.

Looking first to FIG. 1, a flow diagram of the present invention is depicted. In one embodiment of the invention, core samples are obtained over substantially the entire wellbore length; however, an important aspect of the present invention is that discrete samples of the earth's formation surrounding a wellbore need only be taken at selected intervals along the length of the wellbore at step 10. One criteria for establishing the sampling intervals is that discrete samples generally be obtained for every formation lithology traversed by the wellbore along its length. Since the mineral composition of the formations surrounding the wellbore can also be used to evaluate geophysical survey data (e.g., seismic survey data), the minimum resolution interval of the geophysical survey data being evaluated establishes another criteria for the sampling interval. Typically seismic data has the finest resolution interval of any geophysical survey technique (approximately 100 ft). In practice, we have found that a sampling interval of one sample every 10 ft adequately addresses the criteria of lithology changes as well as the geophysical survey minimum resolution interval criteria so as to address the problems of heterogeneous rather than homogeneous earth formations so that the mineral composition of the samples obtained at step 50 below can be correlated with geophysical survey data without introducing sampling bias.

To prepare the samples for step 20, a portion of each sample is ground with a hammer in a metallic crucible to a size of less than 1/32 of an inch. The ground sample is then pulverized for approximately 20–30 minutes in a ball mill. After ball milling, the powdered sample can then be ground finer using a mortar and pestle. When the grinding is complete, the rock sample should have no discernible grains left. Preferably, the grain size of the powered sample should be less than the wavelength of a probing electromagnetic beam used to ascertain the mineral composition of the sample. The powdered sample can then be heated in a vacuum for a period of time to drive off all free moisture. The dried and finely powdered sample is then mixed with dried salt such as potassium bromide in a fixed proportion for all samples. Salt employed should be transparent to the probing electromagnetic radiation in the wavelengths of interest. The salt and powdered sample pellet is then produced in a pressurized die assembly.

At step 20, the sample pellets are mounted in a specimen carrier and inserted into a sample chamber of an electromagnetic spectral analysis instrument. While several types of transmission, reflection and absorption spectral analysis instruments are available (for example, X-ray diffraction, X-ray fluorescence, and infrared absorption), we have found that a Fourier transform infrared spectrometer (FTIR) type instrument is preferable because of its ease and speed of operation. Typical X-ray instrumentation requires water cooling for the X-ray source and are very bulky and can take up to one hour to obtain results. Consequently, field deployment of the present invention generally precludes the use of X-ray instrumentation. The FTIR irradiates each sample with infrared radiation for a period of approximately 60 seconds.

Figure 2:
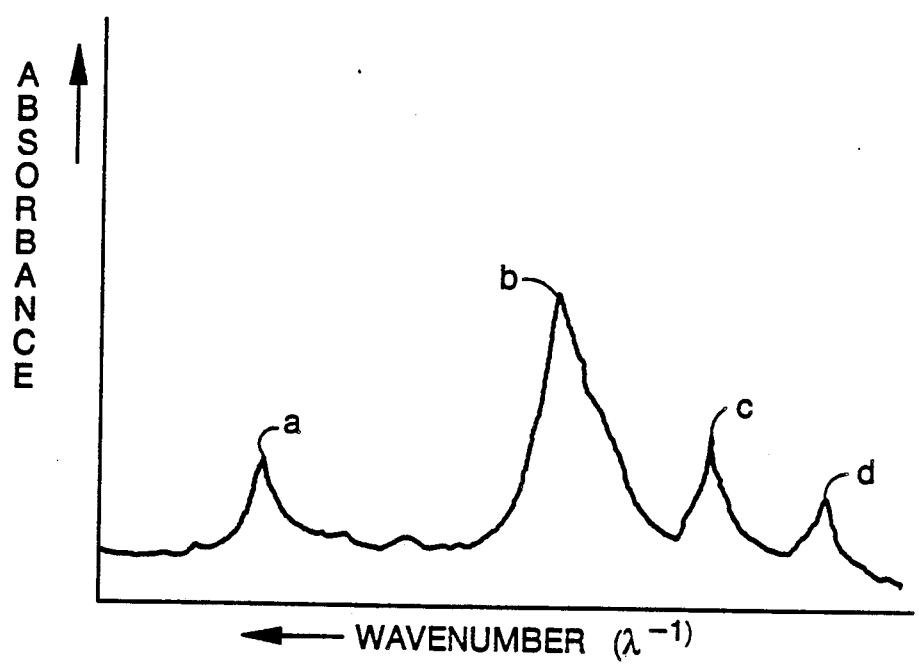
FIG. 2 is a representation of a spectral absorption signal.

As the result of irradiating the sample with infrared radiation, a spectral response signal can be recorded at 30 whereby a measure of the sample's absorption of selected wavelengths of the infrared radiation is obtained. A representation of a spectral response signal is shown in FIG. 2. At step 40, the spectral location and relative amplitude of the characteristic peaks of the spectral response signal are obtained (as indicated in FIG. 2). The characteristic peaks can then be correlated with minerals exhibiting similar infrared characteristic response peaks at 50. For example, the peaks A, B, C, and D can each represent a different mineral. We have found it most advantageous to have a computer (not shown) receive the spectral response signals to locate the characteristic peaks and correlate the characteristic peaks with a stored table of infrared characteristic peaks of a wide array of minerals to identify the minerals represented by the spectral response signals of each sample.

Figure 3:
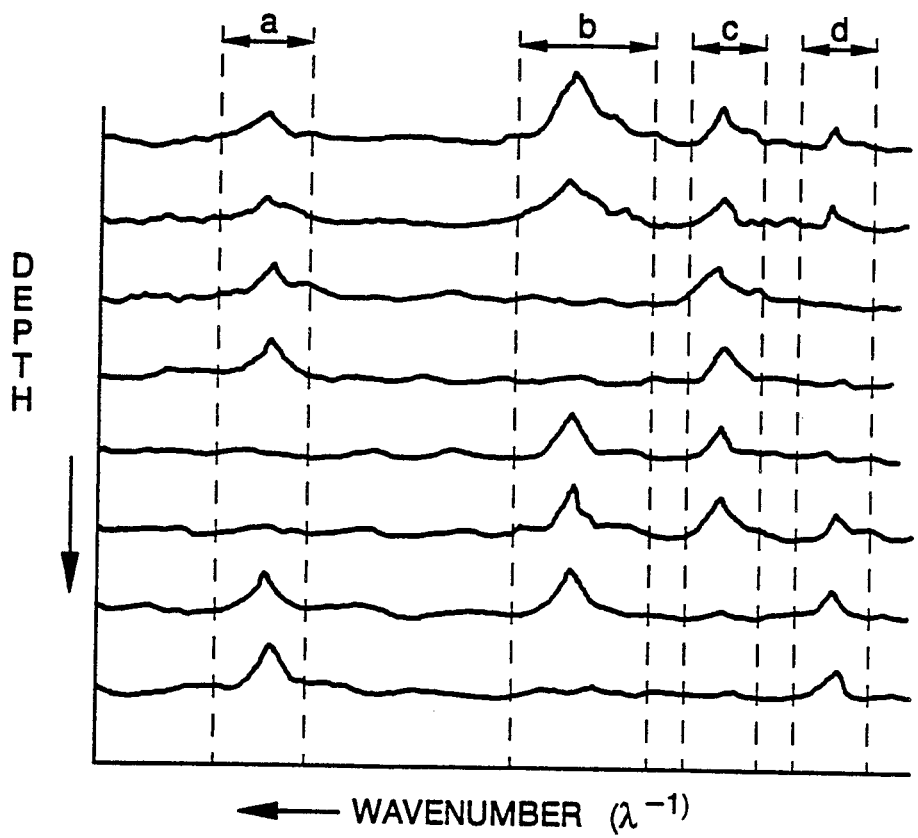
FIG. 3 is a waterfall plot of a plurality of spectral absorption signals as a function of depth.
Figure 6:
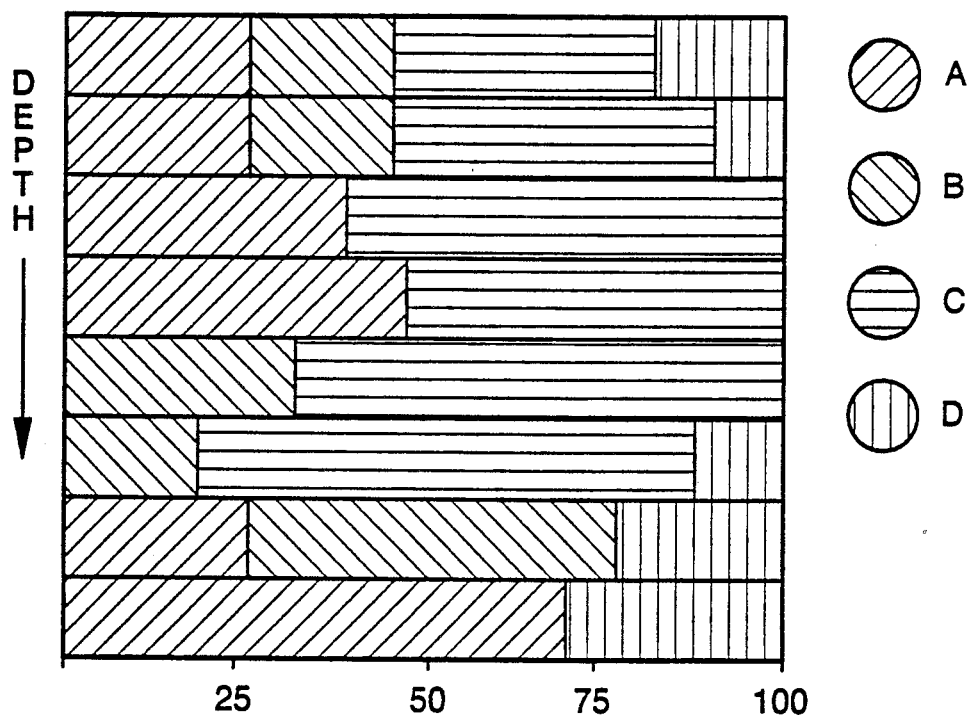
FIG. 6 is a composition log of the minerals comprising the formation surrounding the wellbore.

At step 60, the minerals identified from step 50, and as depicted in FIG. 2, can be displayed as a composition log of the minerals comprising the formations surrounding the wellbore as a function of depth. Such display can be output to a CRT screen of a computer system, a plotter, or a printer. Representative of such displays are FIGS. 3, 4, and 6. In particular, FIG. 3 is a waterfall plot representation of a series of spectral response signals plotted adjacent one another in depth sequence in which the characteristic peaks A, B, C, and D of FIG. 2 can be seen to occur in various combinations as a function of depth. To highlight those segments of the spectral response signals which can be correlated with selected minerals, color bands encompassing a selected range of wavelengths can be overlaid on the display of FIG. 3 as indicated by the separate dashed lines. The occurrence of a peak on the spectral response signal within a color band indicates the presence of a particular mineral. FIG. 4 represents a composition log obtained from the spectral response signals from an actual well. An alternative display can be produced as shown in FIG. 6 which is simply a plot of the various minerals identified as a function of depth with each mineral either color-coded, color shade-coded or indicated by separate symbol.

By observing the relative amplitude and spectral location of such characteristic peaks in each spectral response signal, one can determine the relative weight percentage of any mineral in a sample. In particular, to determine the relative amount of a mineral G in an unknown sample, the relative amplitudes $I_s$ and spectral location of the characteristic peaks in a spectral response signal of an unknown sample can be compared to relative amplitudes $I_o$ and spectral locations of the characteristic peaks in a spectral response signal of the pure mineral G. The ratio of such relative amplitudes $I_s/I_o$ varies with the concentration of mineral G in the sample and can depend markedly on the other elements present and cannot, in general, be predicted by calculation. It is, therefore, necessary to establish the variation by obtaining measurements on a plurality of samples of known composition and through a regression analysis determine the relative amount of mineral in a sample. Such quantitative mineralogy information can then be displayed by varying the width of the line segment representing a particular mineral as depicted in FIG. 6.

Figure 5:
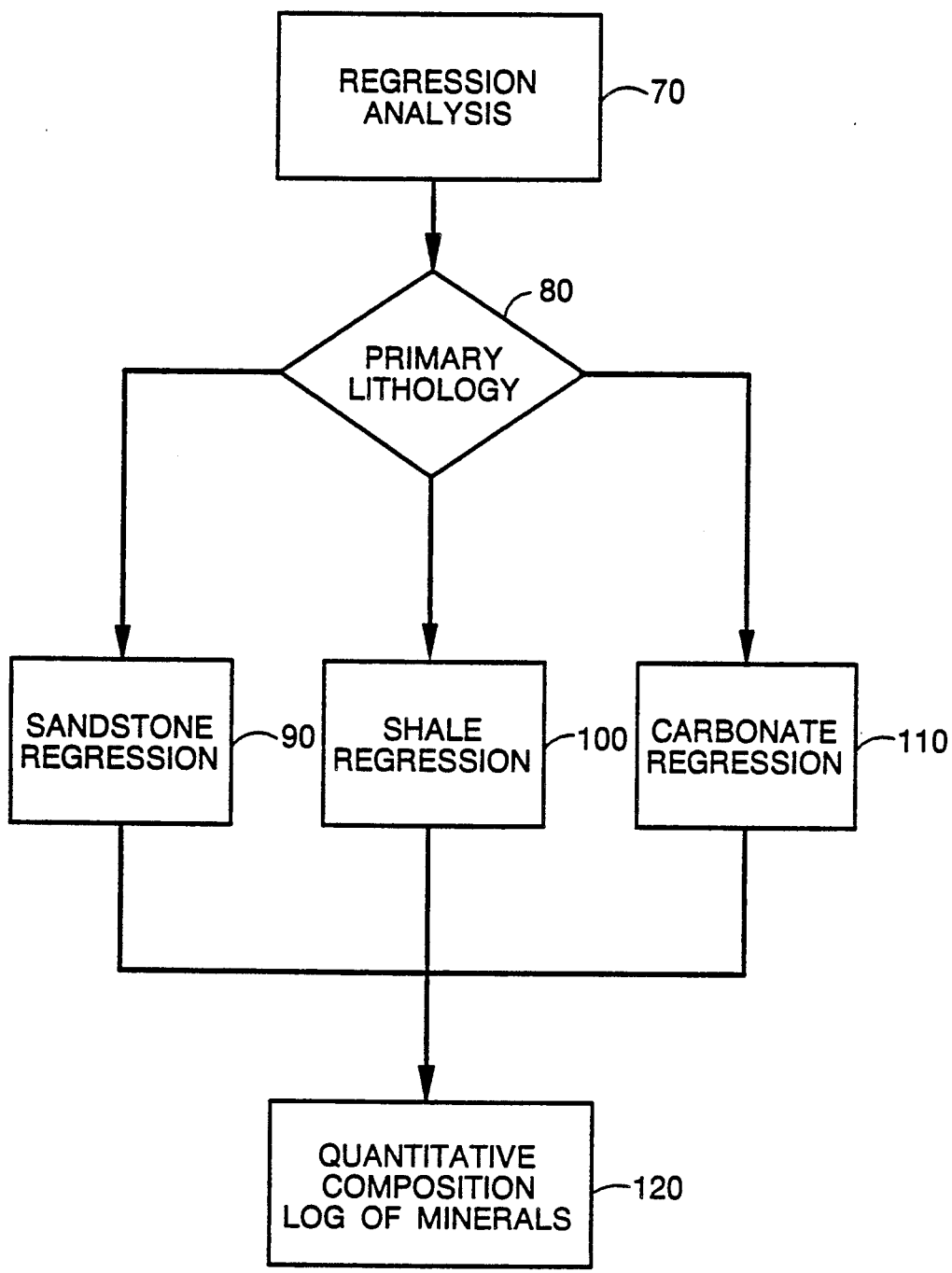
FIG. 5 is a flow diagram for obtaining a quantitative measure of minerals in samples of formations surrounding the wellbore.

With reference now to FIG. 5, a method for obtaining a quantitative measure of the minerals comprising the formations surrounding the wellbore is depicted. At step 70, a plurality of standard samples having known weight percentages of the basic lithologies of interest, i.e., sandstone, shale, and carbonates are prepared. A set of regression coefficients are established for the standard samples. These regression coefficients describe the attributes of spectral peak location such as amplitude, slope, area, moment, and skewness as a function of varying lithologies. At step 80, the regression coefficients for the lithologies are evaluated to determine which set provides the best fit with the spectral response peak attributes for the sample. The decision at step 80 is premised on the major mineral comprising the lithologies of interest, i.e., quartz in sandstone, clays in shales, calcites and dolomites in carbonates. Having identified the primary lithology or mineral constituents of the sample, one of a set of three separate regression analyses are concluded at 90, 100 and 110. In particular, the regression coefficients in each of these separate steps were obtained employing samples of known mineral compositions in which the identified mineral was the primary mineral contained in the sample. For example, the shale regression coefficient can be made when clays comprise at least 20% of the sample. Using these two step processes, a more accurate measurement of relative amount of a mineral in a sample can be obtained. At step 120, a quantitative composition log similar to FIG. 6 can be produced. The scale in FIG. 6 is in relative weight percent from 0 to 100%.

Having described the method and system of the present invention, it is to be understood that various modifications or changes may be made without departing from the scope of the invention as set forth in the claims below.

We claim:

1. A method of evaluating the composition of minerals comprising the formations surrounding a wellbore, comprising the steps of:
    (a) obtaining a plurality of core samples of the earth's formations at selected intervals, corresponding to the minimum resolution interval of a selected geophysical method of survey, along the wellbore length;
    (b) irradiating a portion of each core sample with electromagnetic radiation and recording a spectral absorption response signal representative of the electromagnetic radiation absorbed by said portion of each core sample;
    (c) locating peaks in each spectral absorption response signal;
    (d) identifying minerals in each core sample by correlating the peaks in each spectral absorption response signal with minerals exhibiting similar electromagnetic characteristic peaks; and
    (e) producing a composition log of the minerals comprising the formations surrounding a wellbore along its length.

2. The method of claim 1 further including the step of obtaining a quantitative measure of the minerals in each core sample.

3. The method of claim 1 wherein the step of obtaining core samples of the earth's formation at selected intervals along the wellbore length comprises obtaining a core sample for each formation lithology traversed by the wellbore along substantially its entire length.

4. The method of claim 1 wherein the electromagnetic radiation is infrared.

5. The method of claim 1 wherein the step of producing a composition log comprises plotting a plurality of spectral absorption response signals adjacent one another in depth sequence.

6. A method for determining a quantitative measure of the minerals comprising the formations surrounding a wellbore, including the steps of:
    (a) obtaining a plurality of core samples of the earth's formations at selected intervals along substantially the entire wellbore length;
    (b) irradiating a portion of each core sample with infrared radiation and recording a spectral absorption response signal of the infrared radiation absorbed by said portion of each core sample;
    (c) locating the peaks in each spectral absorption response signal;
    (d) determining the relative amplitude of each peak in the spectral absorption response signal and
    (e) performing a regression analysis using the spectral location and relative amplitudes of the spectral absorption response signals using spectral locations and relative amplitudes for standard samples having a plurality of known mineral compositions to determine a quantitative measure of the minerals present in each core sample.

7. The method of claim 6, further including the step of:
    (a) obtaining sets of characteristic amplitude values and spectral locations for standard samples having a plurality of known weight percentages of selected lithologies; and
    (b) obtaining a set of regression coefficients for each standard sample.

8. A method of evaluating the composition of minerals comprising the formations surrounding a wellbore, comprising the steps of:
    (a) obtaining a plurality of core samples of the earth's formations at selected intervals along substantially the entire wellbore length;
    (b) irradiating a portion of each core sample with infrared radiation and obtaining a Fourier transform absorption response signal representative of the infrared radiation absorbed by said portion of each core sample;
    (c) locating peaks in each Fourier transform response signal;
    (d) identifying minerals in each core sample by correlating the peaks in each Fourier transform absorption response signal with minerals exhibiting similar characteristic absorption peaks; and
    (e) producing a composition log of the minerals comprising the formations surrounding the wellbore along substantially its entire length from the minerals identified from core samples obtained at selected intervals along the wellbore length.

9. The method of claim 8 further including the step of obtaining a quantitative measure of the minerals in each core sample.

10. The method of claim 8 wherein the step of obtaining core samples of the earth's formation at selected intervals along the wellbore length comprises obtaining a core sample for each formation lithology traversed by the wellbore along its length.

11. The method of claim 8 wherein the step of obtaining core samples of the earth's formation at selected intervals along the wellbore comprises obtaining core samples at intervals corresponding to a minimum resolution interval of a selected geophysical method of survey.

12. The method of claim 8 further including producing a quantitative mineral composition log of the minerals comprising the formations surrounding the wellbore along substantially its entire length.

13. The method of claim 8 wherein the step of producing a composition log comprises plotting a plurality of spectral absorption response signals adjacent one another in depth sequence.

14. A method for determining a quantitative measure of minerals comprising a formation surrounding a wellbore, including the steps of:
    (a) obtaining a plurality of core samples of the earth's formation at selected intervals, corresponding to the minimum resolution intervals of a selected geophysical method of survey, along a wellbore length;
(b) irradiating a portion of each core sample with electromagnetic radiation and recording a spectral absorption response signal of the electromagnetic radiation absorbed by said portion of each core sample;
(c) locating peaks in each spectral absorption response signals;
(d) determining the relative amplitude of each peak int eh spectral absorption response signal; and
(e) performing a regression analysis using the spectral location and relative amplitude of the spectral absorption response signals using spectral locations and relative amplitudes for standard samples having a plurality of known mineral compositions to determine a quantitative measure of the minerals present in each core sample.

* * * * *